(12) United States Patent
Badaoui et al.

(10) Patent No.: US 11,951,230 B2
(45) Date of Patent: Apr. 9, 2024

(54) DEVICE FOR GUIDED BONE REGENERATION AND PRODUCTION METHOD

(71) Applicant: ZIRBONE, Paris (FR)

(72) Inventors: Ralphe Badaoui, Paris (FR); Joseph Nammour, Paris (FR)

(73) Assignee: ZIRBONE, Paris (FR)

( * ) Notice: Subject to any disclaimer, the term of this patent is extended or adjusted under 35 U.S.C. 154(b) by 0 days.

(21) Appl. No.: 17/415,947

(22) PCT Filed: Dec. 17, 2019

(86) PCT No.: PCT/EP2019/085686
§ 371 (c)(1),
(2) Date: Jun. 18, 2021

(87) PCT Pub. No.: WO2020/127291
PCT Pub. Date: Jun. 25, 2020

(65) Prior Publication Data
US 2022/0040372 A1  Feb. 10, 2022

(30) Foreign Application Priority Data
Dec. 20, 2018  (EP) .................................. 18306770

(51) Int. Cl.
*A61L 27/10* (2006.01)
*A61C 13/00* (2006.01)
(Continued)

(52) U.S. Cl.
CPC .......... *A61L 27/10* (2013.01); *A61C 13/0004* (2013.01); *A61L 27/105* (2013.01);
(Continued)

(58) Field of Classification Search
CPC .... A61L 27/10; A61L 27/105; A61L 2430/02; A61C 13/0004; B33Y 80/00; B33Y 50/00; B28B 1/001
See application file for complete search history.

(56) References Cited

U.S. PATENT DOCUMENTS 6,302,913 B1 * 10/2001 Ripamonti ............... A61L 27/12
623/23.76
6,712,851 B1 * 3/2004 Lemperle ........... A61B 17/8085
606/154
(Continued)

FOREIGN PATENT DOCUMENTS

| CN | 1605654 A | 4/2005 |
|---|---|---|
| CN | 1669538 A | 9/2005 |

(Continued)

OTHER PUBLICATIONS

Jonas Anderud, et al., Guided bone augmentation using ceramic space-maintaining devices: the impact of chemisty, Mar. 12, 2015, Dovepress, Clinical, Cosmetic and Investigational Dentistry, pp. 1-9 (Year: 2015).*

(Continued)

*Primary Examiner* — Monica A Huson
*Assistant Examiner* — Kelsey C Grace
(74) *Attorney, Agent, or Firm* — CANTOR COLBURN LLP

(57) ABSTRACT

The present invention relates to a device for guided bone regeneration, intended for the reconstruction of a buccal bone defect, composed of zirconium dioxide and having a shape which covers said buccal bone defect. The present invention also relates to a method for producing a device of the invention, comprising a step of constructing the device (Continued)

of the invention according to a three-dimensional representation obtained by means of a technique of maxillo-dental imaging of the bone defect.

5 Claims, 5 Drawing Sheets

(51) Int. Cl.
    *B33Y 50/00*     (2015.01)
    *B33Y 80/00*     (2015.01)
    *B28B 1/00*     (2006.01)

(52) U.S. Cl.
    CPC ............... *B33Y 50/00* (2014.12); *B33Y 80/00* (2014.12); *A61L 2430/02* (2013.01); *B28B 1/001* (2013.01)

(56) References Cited

U.S. PATENT DOCUMENTS

2005/0192675 A1    9/2005    Robinson
2009/0118114 A1    5/2009    Zhang

FOREIGN PATENT DOCUMENTS

| | | |
|---|---|---|
| CN | 108606851 A | 10/2018 |
| CN | 108888379 A | 11/2018 |
| CN | 212853732 U | 4/2021 |
| RU | 2572355 C1 | 1/2016 |
| WO | 9114404 A1 | 10/1991 |
| WO | 2009052429 A1 | 4/2009 |
| WO | 2013095077 A1 | 6/2013 |

OTHER PUBLICATIONS

International Search Report for corresponding application PCT/EP2019/05686 filed Jun. 25, 2020; dated Jan. 29, 2020.

Jonas Anderud on "Guided Bone Regeneration using Ceramic Membranes", Doctoral Dissertation in Odontology, Jan. 1, 2016, XP55597214.

Jonas Anderud, "Guided bone augmentation using ceramic space-maintaining devices: the impact of chemistry", Clinical, Cosmetic and Investigational Dentistry 2015: 7 45-53.

Response to EPO Search Opinion for corresponding application EP18306770.1; Response dated Sep. 4, 2020.

* cited by examiner

A/

B/

C/

A/

B/

C/

A/

B/

C/

DEVICE FOR GUIDED BONE REGENERATION AND PRODUCTION METHOD

TECHNICAL FIELD

The present disclosure relates to a guided bone regeneration device intended for the reconstruction of an oral bone defect, and to a method for manufacturing such a device.

Thus, the present disclosure finds applications in the field of medicine, and more particularly in the field of dental surgery.

In the description below, the references between square brackets ([ ]) refer to the list of references given at the end of the text.

BACKGROUND

In order to regenerate tissue that has been destroyed and/or that has disappeared as a result of bone loss, there are a number of bone augmentation techniques, such as apposition grafts, interposition grafts, expansion, distraction, sinus grafts or else guided bone regeneration (GBR).

The purpose of GBR is to recreate bone so that a dental implant can be fitted and/or stabilized, or so as to recreate a ridge for a non-removable prosthesis. Conventionally, a membrane is positioned between the bone and the gum, for 3 to 6 months, before the implant can be used or the non-removable prosthesis can be created. The membrane used forms a physical barrier on the one hand preventing the bone defect from becoming colonized with conjunctive and epithelial soft tissue and on the other hand restricting access to the wound space to only those cells capable of osteogenesis. These membranes thus have a triple role: they prevent the growth of cells from the covering mucus membrane and encourage the migration of cells from the medullary spaces into the clot inhabiting the site, they stabilize the bone graft and the clot and they stabilize the filling with biomaterial.

In this context, there are a number of membrane types, resorbable or non-resorbable, that are used, such as, for example, membranes made from polytetrafluoroethylene (PTFE) or from resorbable collagen. The characteristics of the non-resorbable membranes are primarily biological inertia, flexibility, chemical stability and asymmetric microporosity. By contrast, they need to be secured using screws and require a second intervention to remove them.

By contrast, resorbable membranes have the advantage of not needing to be removed after bone regeneration, thereby avoiding potential irritation of the tissues that could occur at the time of removal, if the membrane has become attached to the surrounding tissue during the healing phase. However, resorbable membranes have the disadvantage of possible interference between resorption/healing and bone regeneration, and require a material to support the membrane.

There is therefore a real need for a device that alleviates these deficiencies, particularly that makes it possible to obtain optimal modeling of the reconstruction and mimicry and symmetry of the bone structure.

BRIEF SUMMARY

The device of the disclosure allows bone augmentation both vertically and horizontally to fill the bone defect, optimal modeling of the reconstruction and mimicry and symmetry of the bone structures.

Thus, a first subject matter of the disclosure relates to a device for guided bone regeneration, intended for the reconstruction of a bone defect. It is made up of zirconium dioxide ($ZrO_2$) and has a shape covering said oral bone defect.

Advantageously, the device of the disclosure has a three dimensional shape at least partially, and preferably completely, covering the bone defect. Thus, at the end of bone reconstruction, the reconstructed volume may be substantially identical to, or even greater than, that caused by the bone loss being treated.

In order to obtain a three dimensional shape covering the shape of the bone defect that is to be treated, any technique for modeling the volume and/or the quantity of bone to be reconstructed can be employed. This may be a technique of dento-maxillary imaging of the bone defect, such as, for example, cone beam volumetric tomography. Advantageously, the bone defect may be digitally schematized using software suitable for quantifying the bone substance to be regenerated, such as, for example, the MIMICS or 3-matic software packages, this list being nonlimiting.

The device of the disclosure is thus manufactured on the basis of the shape that has been modeled, so as to mimic the 3D plan, using any suitable technique known to those skilled in the art such as, for example, molding, machining or 3D printing. Possibly, starting from the pattern, an additional layer 1 mm thick may be added to the 3D representation, before the device of the disclosure is constructed, in order advantageously to mitigate the effects of superficial epithelial formation which may occur in certain regenerations.

Advantageously, the device of the disclosure has an appropriate shape that allows it to cover all or part of the bone defect and allows the reconstruction of the entire bone volume lost, if necessary. Advantageously, whatever the shape chosen, the device creates a hollow space, when it is installed, between the wall of the device and the residual bone, so as to allow biomaterial to be introduced into the device of the disclosure. Any shape that makes it possible to achieve this objective can be employed by those skilled in the art. This may for example be a shape selected from a shell, a rigid plate, a cup and a net (also known as a mesh).

As stated previously, the device of the disclosure is composed of zirconium dioxide (also known as zirconia or zirconium oxide). The zirconium dioxide content of the device may for example be comprised between 88% and 96%, for example 88%, or 89%, or 90% or 91% or 92% or 93% or 94% or 95% or 96%. Advantageously at least one other constituent conventionally present in this type of ceramic may be present, such as for example yttrium oxide, hafnium oxide and/or aluminum oxide. For example, yttrium oxide may be present at a content of 4 to 6%, hafnium oxide may be present at a content of 1-5%, and aluminum oxide may be present at a content of 0 to 1%. This may for example be a commercially available composition, such as, for example, Zfx™ Zirconia (Zfx GmbH, Germany). Advantageously, the zirconium dioxide is used in the device of the disclosure for its known physical properties, such as its breaking strength and resistance to cracking, its high level of biocompatibility, its neutrality, and the fact that it causes very little inflammation. Advantageously, zirconia constitutes a cell and tissue barrier. In addition, it is advantageously not osteointegratable and is easy to remove. By virtue of the features of the device of the disclosure, the graft is advantageously stabilized and compressed, and exhibits a near-zero level of resorption.

Advantageously, the device of the disclosure may comprise at least one perforation to stabilize the device, each perforation being intended to receive an osteosynthesis screw. In this respect, the perforation or perforations is/are made in the vestibular wall of the device. The number of perforations may be determined according to conventional criteria applied in this field, for example according to the size of the bone defect. In this respect there may be a number of perforations comprised between 1 and 4 or even between 1 and 20, or even more, depending on what is required and on the volume that is to be reconstructed.

Advantageously, the device may further comprise microperforations over all or part of its wall. The microperforations may be distributed over said wall uniformly or irregularly. The microperforations may have a diameter comprised between 1 μm and 1 mm, 1 mm preferably being excluded, for example between 2 μm and 800 μm, or between 5 μm and 500 μm, or between 10 μm and 300 μm. The density of the microperforations on the wall may be comprised between 1 and 100 microperforations per square centimeter, for example between 20 and 90, or between 30 and 80. The holes are ordinarily round, but may be of any other shape compatible with their function, for example square, oval or rectangular in shape. Advantageously, the microperforations may make it possible to improve angiogenesis during tissue regeneration. This is because the microperforations may allow the neovascularization to access the biomaterial from the soft tissue, in addition to that which arrives via the native bone or via the native ridge to be augmented. The microperforations may also improve adhesion between the soft tissue and the zirconia plate, thus avoiding tension around the sutures and reducing initial and late exposure of the device. The microperforations may be produced by any method or tool known to those skilled in the art, for example using a fine milling cutter or a laser.

Advantageously, the device of the disclosure may comprise at least one window created in its wall, notably intended for the insertion and condensation of a biomaterial. The biomaterial, once inserted between the bone and the wall of the device of the disclosure, namely in the space that is to be reconstructed, will allow osteoinduction and thus reconstruct the desired bone. Any type of biomaterial suitable for bone reconstruction can be employed in this context, such as any type of bone substitute selected from allogenic, xenogenic, autogenic and synthetic bone substitutes, this list being nonlimiting. The size, shape and number of windows may be selected by the person skilled in the art notably according to the size of the device of the disclosure and according to the nature of the bone defects to be treated. For example, the window may be square, round, oval or rectangular in shape. It may for example be inscribed inside a rectangle measuring 1 to 20 mm tall by 1 to 30 mm wide or more. The window may be designed according to any suitable technique known to those skilled in the art, for example using a 3D planner. The number of windows may be comprised between 1 and 5, and may for example be 1, 2, 3, 4 or 5. However, the number of windows may be adapted by the person skilled in the art according to their requirements. The window or windows may be stabilized by a fixing device, such as an osteosynthesis screw, wires, meshing or nesting. Advantageously, the purpose of a window is to allow the chamber or space created by the device to be filled with biomaterials and to allow the latter to be compacted during the addition and during the fixing of the window. The window is fixed upon an aperture formed in the body through which the biomaterial is passed into the chamber or space within the device. When the window is in an open position, the aperture is exposed and the biomaterial may be inserted into the chamber or space. In a closed position, the window occludes the aperture to contain the biomaterial within the volume and to allow for the condensation thereof.

The device may have a thickness suited to its purpose, namely of protecting the biomaterial for the time necessary for bone reconstruction. In this regard, a person skilled in the art may readily determine the suitable thickness according to the circumstances. For example, the thickness of the device of the disclosure may be comprised between 0.1 mm and 2.5 mm, for example may be around 0.1 mm, or 0.2 mm, or 0.3 mm, or 0.4 mm, or 0.5 mm, or 0.6 mm or 0.7 mm or 0.8 mm or 0.9 mm or 1.0 mm or 1.1 mm or 1.2 mm or 1.3 mm or 1.4 mm or 1.5 mm or 1.6 mm or 1.7 mm or 1.8 mm, or 1.9 mm, or 2.0 mm, or 2.1 mm, or 2.2 mm, or 2.3 mm, or 2.4 mm, or 2.5 mm.

Advantageously, the device of the disclosure is easy to remove once it has been in place for the time necessary for bone reconstruction. Specifically, as it covers, from the outside, the volume that is to be reconstructed, it need merely be lifted off once the screw or screws has/have been removed.

Advantageously, the device of the disclosure may further and optionally comprise perforations in the ridge region to allow the insertion of dental implants during the surgical step of guided bone regeneration.

Another subject matter of the disclosure relates to a method for manufacturing a device of the disclosure as described hereinabove. The method employed may notably comprise a step of constructing said device on the basis of a 3D representation of the bone defect which representation is obtained by a dento-maxillary imaging technique, for example by a cone beam volumetric tomography technique.

Advantageously and as indicated hereinabove, the 3D representation of the bone defect may be digitally schematized using a software package suitable for quantifying the bone substance to be regenerated.

The digital schematization potentially makes it possible to obtain a pattern, from which the device of the disclosure will be manufactured so as to cover the 3D representation of the bone defect. It is potentially possible to add an additional layer 1 mm thick, so as to increase the volume that is to be covered and obtain a higher reconstructed volume and mitigate against the formation of a superficial epithelial layer.

Another subject matter of the disclosure relates to a bone regeneration method comprising the steps of:
 fitting a device according to the disclosure at the site of a bone defect of a patient,
 introducing biomaterial into the device,
 leaving the device fitted for enough time for the biomaterial to condense, and
 removing the device of the disclosure.

Further advantages may also become apparent to a person skilled in the art on reading the examples below, which are illustrated by the attached figures given by way of illustration.

EXAMPLES

Figure 1:
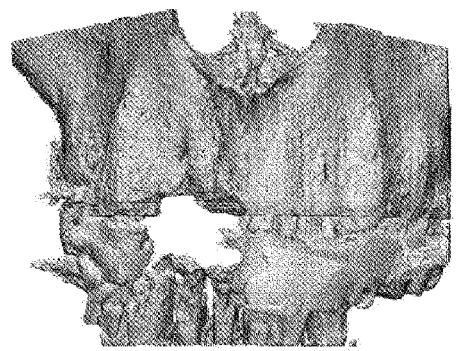
FIG. 1 depicts a bone volumetric reconstruction schematized in three dimensions. A: face-on view of the volume to be reconstructed. B: view from above of the volume that is to be reconstructed. C: view from below of the volume that is to be reconstructed.
Figure 1:
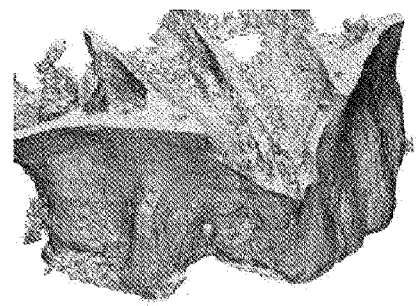
Figure 1:
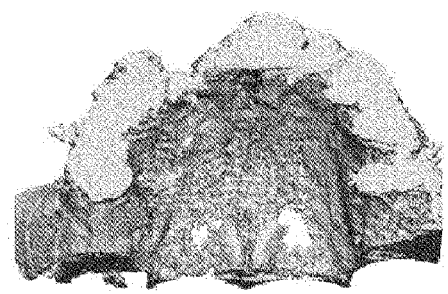
Figure 2:
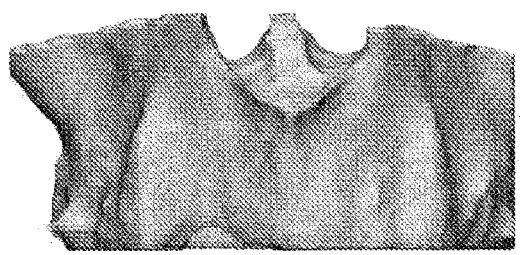
FIG. 2 depicts a view of the bone volume to be reconstructed, after cleaning and definition of the fill volume through a mirroring effect. A: face-on view of the volume to be reconstructed. B: view from above of the volume to be reconstructed. C: view from beneath of the volume to be reconstructed.
Figure 2:
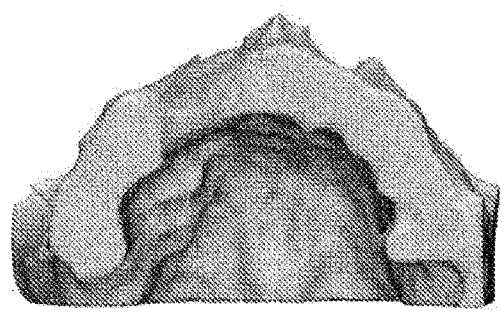
Figure 2:
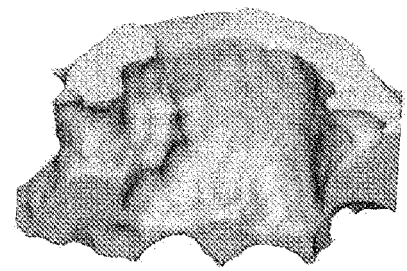
Figure 3:
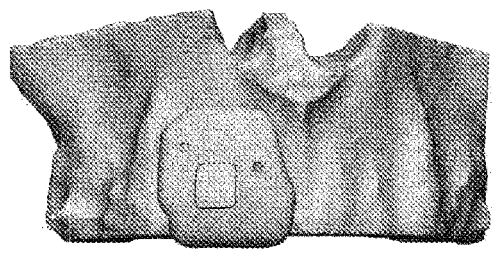
FIG. 3 depicts a view of a cup that is 0.8 mm thick with a 1 mm offset above the volume that is to be filled. A: face-on view of the volume that is to be reconstructed. B: view from above of the volume that is to be reconstructed. C: face-on view of the volume that is to be reconstructed.
Figure 3:
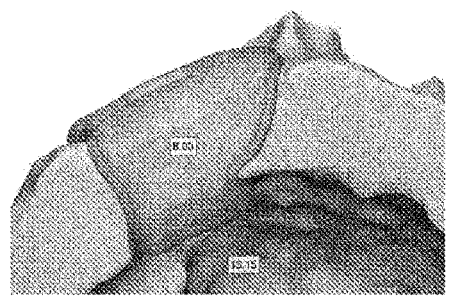
Figure 3:
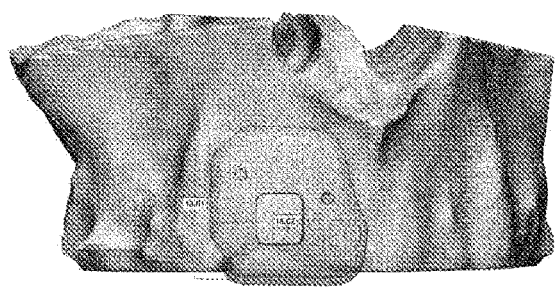
Figure 4:
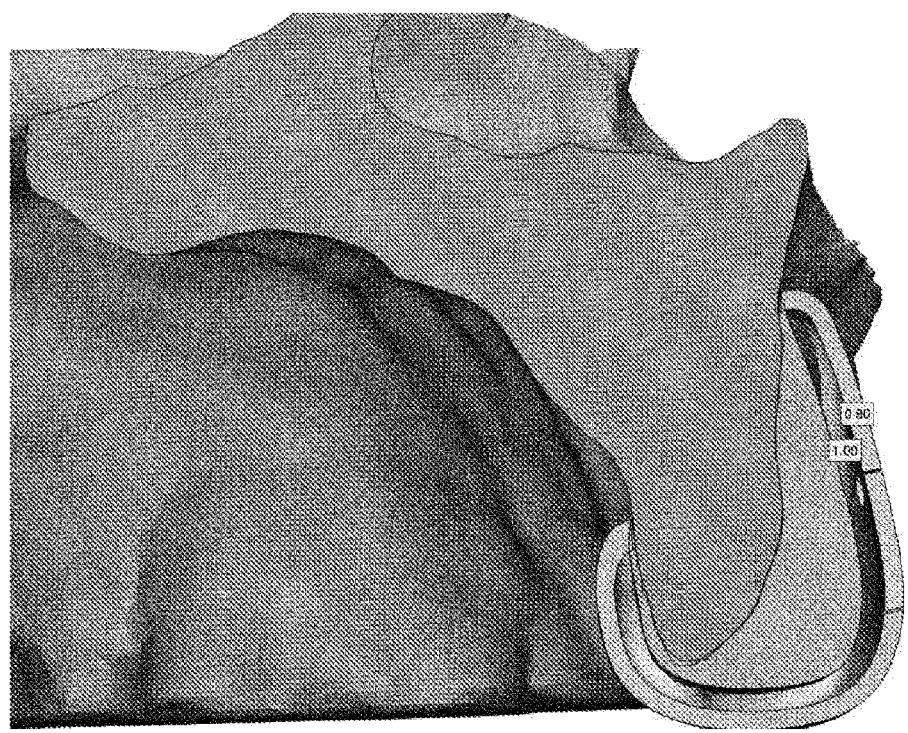
FIG. 4 depicts a view in cross section of a shell covering the bone volume that is to be reconstructed.
Figure 5:
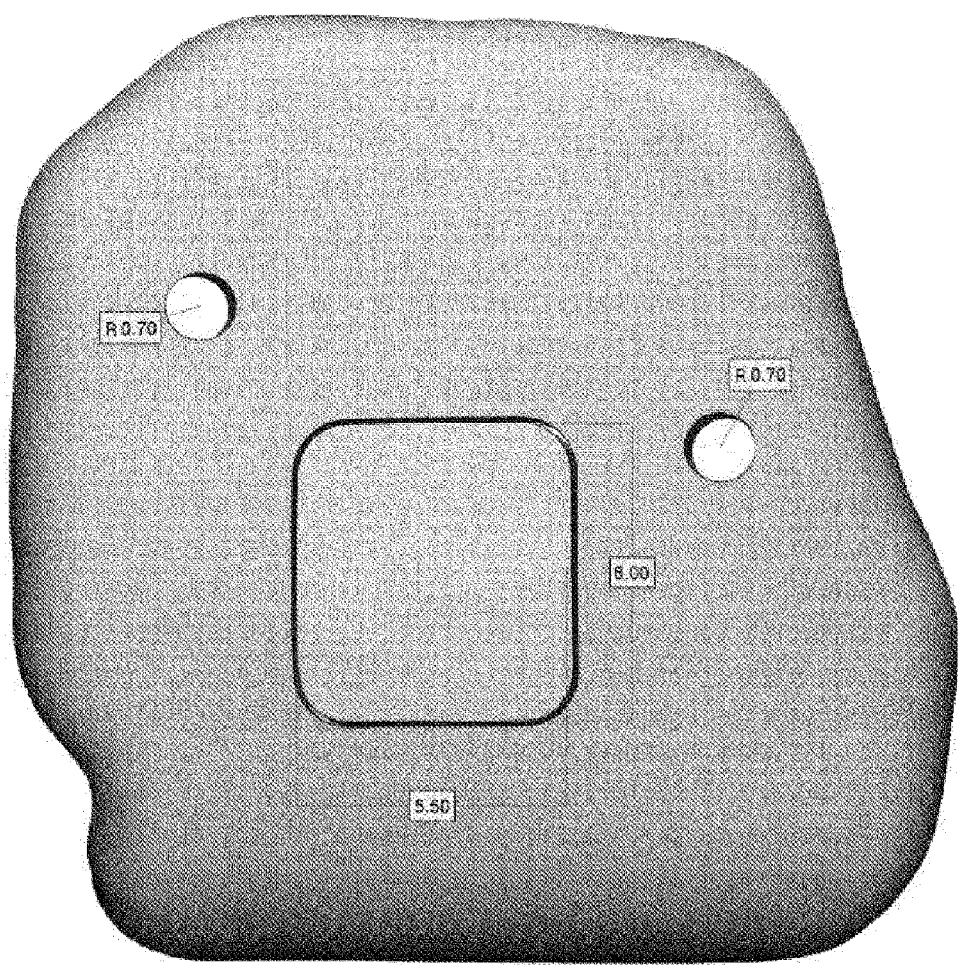
FIG. 5 depicts a face-on view of a shell comprising a window measuring 6 mm tall by 5.5 mm wide, and two fixing holes each with a diameter of 1.4 mm.

Example 1: Preparation of a Device in the Form of a Shell Intended for Guided Bone Regeneration A model of the volume of the quantity of bone to be reconstructed is created using cone beam volumetric tomography.

A 3D representation of the reconstruction of the bone defect is digitally schematized using the MIMICS/3-matic software package so as to quantify the bone substance to be regenerated.

Using this pattern, an "optional" additional layer 1 mm thick is added to the 3D representation, then a shell 0.6 to 1.8 mm thick is designed so that it covers the 3D plan mentioned.

Perforations are designed so as to stabilize the future zirconia shell using osteosynthesis screws.

Once the shell pattern has been validated, the shell is printed in zirconia using a 3D printer.

Example 2: Example of Use of the Guided Bone Regeneration Device

The patient was prescribed preoperative medication: clavulanic amoxicillin acid (2 g per day), and prednisolone (60 mg per day).

Paracetamol/codeine and mouthwash (0.12 chlorexidine) were prescribed for after the operation.

The procedure was carried out under local anesthetic Ubistesine® with 1:200000 vasoconstrictor.

Decontamination with Betadine® was performed intra- and extra-orally. A supra-crestal and then intra-sulcular incision were made with a 15 C scalpel blade to end in two oral release incisions. A complete strip of tissue was lifted up, then the strip was released after the periosteal incisions. The strip was dissected using a pair of Metzenbaum® dissecting scissors.

The customized zirconia shell/mesh was positioned. Holes were bored through the holes in the existing envelope. The two osteosynthesis screws were partially screwed in, then the allogenic biomaterials were placed under the cup. The screws were tightened to ensure the stability of the biomaterial. Sutures were applied, edge to edge, without tension.

The invention claimed is:

1. A device for guided bone regeneration for reconstruction of an oral bone defect, comprising:
    a body composed of zirconium dioxide and having a shape configured to cover said oral bone defect and to create a volume between the body and the oral bone defect; and
    a window arranged at an aperture in a wall of the body configured for insertion and condensation of a biomaterial through the window into the volume;
    wherein the window comprises an open position in which the aperture is exposed to allow for the insertion of the biomaterial through the aperture into the volume, and a closed position in which the aperture is occluded to contain the biomaterial in the volume and to allow for the condensation.

2. The device as claimed in claim 1, wherein the body comprises at least one other constituent selected from yttrium oxide, hafnium oxide and aluminum oxide.

3. The device as claimed in one of claim 1, wherein the shape of the body is selected from a shell, a plate and a net.

4. The device as claimed in claim 1, wherein the body comprises at least one perforation for stabilizing said device, said perforation being intended to receive an osteosynthesis screw.

5. The device as claimed in claim 1, wherein the wall has a thickness comprised between 0.6 mm and 1.8 mm.

\* \* \* \* \*